United States Patent
Lan et al.

(10) Patent No.: US 12,080,186 B2
(45) Date of Patent: Sep. 3, 2024

(54) HIGH-SPEED REMOTE LANDSLIDE SIMULATION TEST DEVICE WITH A VARIABLE ANGLE

(71) Applicant: Chang'an University, Xi'an (CN)

(72) Inventors: Hengxing Lan, Xi'an (CN); Mervyn Lan, Xi'an (CN); Zhao Chen, Xi'an (CN); Shijie Liu, Xi'an (CN); Weifeng Sun, Xi'an (CN); Ning Zhang, Xi'an (CN); Bei Zhang, Xi'an (CN)

(73) Assignee: CHANG'AN UNIVERSITY, Xi'an (CN)

( * ) Notice: Subject to any disclaimer, the term of this patent is extended or adjusted under 35 U.S.C. 154(b) by 0 days.

(21) Appl. No.: 18/533,177

(22) Filed: Dec. 8, 2023

(65) Prior Publication Data
US 2024/0105083 A1     Mar. 28, 2024

Related U.S. Application Data

(63) Continuation of application No. PCT/CN2023/119367, filed on Sep. 18, 2023.

(30) Foreign Application Priority Data

Sep. 26, 2022 (CN) .......................... 202211175112.1

(51) Int. Cl.
    *G01N 33/24*     (2006.01)
    *G09B 25/04*     (2006.01)

(52) U.S. Cl.
    CPC ........... *G09B 25/04* (2013.01); *G01N 33/246* (2013.01)

(58) Field of Classification Search
CPC ....... G01N 33/24; G01N 33/246; G09B 25/04
See application file for complete search history.

(56) References Cited

U.S. PATENT DOCUMENTS

| | | | |
|---|---|---|---|
| 2016/0047724 A1* | 2/2016 | Jeong | G01N 3/24 73/784 |
| 2019/0113496 A1* | 4/2019 | Tang | G01N 33/246 |

FOREIGN PATENT DOCUMENTS

| | | | |
|---|---|---|---|
| CN | 108387714 A | * | 8/2018 |
| CN | 109991393 A | * | 7/2019 |

(Continued)

OTHER PUBLICATIONS

CN-108387714-A (Year: 2018).*

(Continued)

*Primary Examiner* — Kristina M Deherrera
*Assistant Examiner* — Fatemeh Esfandiari Nia

(57) ABSTRACT

A high-speed remote landslide simulation test device with a variable angle includes a support adjustment component, slide plates, and loose leaves. The device first transmits the operation paths of adjusting the slide plate at different angles to the controller, and the personnel operates the control panel to control the support jack, the motor, and the electromagnet to start and stop through the controller, the output shaft of the motor drives the stainless steel threaded rod to rotate, the controller first energizes one electromagnet and disconnects the other three electromagnets, which can only make the stainless steel threaded rod rotate in a fixed position inside the inner threaded pipe, and the three inner threaded pipes follow the rotation direction of the stainless steel threaded rod, thus, the position of the support jack can be moved separately.

9 Claims, 6 Drawing Sheets

(56) References Cited

FOREIGN PATENT DOCUMENTS

| CN | 213780086 | U | * | 7/2021 | |
|---|---|---|---|---|---|
| CN | 111354255 | B | * | 8/2021 | ............ G01N 33/24 |
| CN | 113419045 | A | * | 9/2021 | |
| KR | 20170081589 | A | * | 7/2017 | |

OTHER PUBLICATIONS

CN-109991393-A (Year: 2019).*
CN-111354255-B (Year: 2021).*
CN-113419045-A (Year: 2021).*
CN-213780086-U (Year: 2021).*
KR-20170081589-A (Year: 2017).*

* cited by examiner

HIGH-SPEED REMOTE LANDSLIDE SIMULATION TEST DEVICE WITH A VARIABLE ANGLE

CROSS REFERENCE TO THE RELATED APPLICATIONS

This application is the Continuation Application of International Application No. PCT/CN2023/119367, filed on Sep. 18, 2023, which is based upon and claims priority to Chinese Patent Application No. 202211175112.1, filed on Sep. 26, 2022, the entire contents of which are incorporated herein by reference.

TECHNICAL FIELD

The invention relates to the field of landslide simulation test technology, in particular to a high-speed remote landslide simulation test device with a variable angle.

BACKGROUND ART

The landslide is a slip geological phenomenon that occurs along the shear failure surface of the slope rock and soil mass, the landslide that occurs in the town often smashes and buries houses, causes human and animal casualties, destroys fields, factories, schools, government buildings, etc., and causes destruction to various facilities, ends up with water, electricity and labor shortage, and sometimes even destroys the entire town, the landslide causes heavy losses to the people's production and life. Therefore, it is necessary to simulate the real field environment through the landslide simulation test, find out the mechanism of landslide occurrence, and provide theoretical support for field landslide early warning work in a better way.

Most of the existing landslide models are less flexible, and it is difficult to adjust the angle of the main body of the landslide quickly, and it is impossible to simulate different mountain conditions in the field. At the same time, most of the existing landslide models can only perform local rainfall or global rainfall in terms of simulated rainfall, and cannot achieve accurate control of the location and intensity of rainfall. Therefore, a high-speed remote landslide simulation test device with a variable angle is proposed.

SUMMARY

In view of the above problems, the invention desires to provide a high-speed remote landslide simulation test device with a variable angle to solve or alleviate the technical problems existing in the existing technology, or at least provide a useful choice.

The technical solution of the embodiment of the invention is realized as follows: a high-speed remote landslide simulation test device with a variable angle, comprising a support adjustment component, slide plates, and loose leaves, the support adjustment component includes a U-shaped plate, support jacks, a controller and a motor;

four support jacks, three slide plates and four loose leaves are provided, four piston rods of the four support jacks are respectively installed with four lower hinges, an inner wall of the lower hinge is installed with a shaft, an outer wall of the shaft is installed with an upper hinge, an upper surface of the upper hinge is installed with a support plate, upper surfaces of the three upper hinges are installed on lower surfaces of the three slide plates respectively, adjacent sides of the three slide plates are installed on outer walls of loose leaves, repulsive sides of the two slide plates are installed on the side of the other two loose leaves respectively, another side of one loose leaf is installed on one side of the support plate, another side of the another loose leaf is installed with a stacking plate, bases of the support jacks are installed with moving bases respectively, one side of the moving base is provided with a through hole, an inner wall of the through hole is rotary connected to an inner threaded pipe through a bearing, the inner wall of the through hole is installed with an electromagnet, an inner wall of the inner threaded pipe is connected to a stainless steel threaded rod, one side of the U-shaped plate is installed with a motor, an output shaft of the motor runs through the side of the U-shaped plate and is installed at one end of the stainless steel threaded rod, an inner wall of the U-shaped plate is installed with an installation plate, the other end of the stainless steel threaded rod is rotary connected to one side of the installation plate through a bearing, one side of the U-shaped plate is installed with a controller.

Furthermore, outer walls of the three slide plates are symmetrically installed with two side plates, upper surfaces of the two side plates are installed with an upper roof, an upper surface of the upper roof is installed with a water storage tank and a water pump respectively, an inlet of the water pump is installed with a pumping pipe, one end of the pumping pipe runs through an upper surface of the water storage tank, an outlet of the water pump is installed with an outlet pipe, one end of the outlet pipe runs through a built-in water pipe network of the upper roof, the built-in water pipe network of the upper roof is evenly installed with spraying nozzles, and the built-in water pipe network of the upper roof is evenly installed with nozzle switches, an outer wall of the outlet pipe is equipped with a water pressure meter and a water pressure adjustment knob respectively, and the spraying nozzles are controlled by adjusting the nozzle switches to spray water to a spraying area on the slide plate.

Furthermore, an upper surface of the support plate is installed with an air storage tank, an outer wall of the air storage tank is penetrated with a vent pipe, one end of the vent pipe is penetrated with a high-speed cylinder, one side of the high-speed cylinder is provided with a piston, the upper surface of the support plate is installed with a cover plate, an upper surface of the cover plate is installed on a lower surface of the high-speed cylinder, and a position of the high-speed cylinder is fixed by the setting of the cover plate.

Furthermore, the upper surface of the support plate is symmetrically installed with two slide rails, and inner walls of the two slide rails slides are slidingly connected to a material cart, it is convenient for the material cart to move through the setting of the slide rail.

Furthermore, the upper surface of the support plate is symmetrically installed with two buffer plates, the material cart is blocked by the buffer plates and stops moving through the setting of the buffer plates, and the landslide material in the material cart continues to move forward into the slide plate due to inertia.

Furthermore, a high-speed camera is installed above the stacking plate, the high-speed camera will record the whole process of the landslide through the setting of the high-speed camera.

Furthermore, the outer wall of the air storage tank is equipped with a barometer and an air compressor respectively, the air is inflated into the air storage tank by starting the air compressor, and when the barometer on the air storage tank shows a set pressure, turn on the regulating switch on the air compressor.

Furthermore, a rear surface of the U-shaped plate is equipped with a control panel, through the setting of the control panel, it is convenient for personnel to control the controller, start and stop the motor, the high-speed camera, the air compressor, the high-speed cylinder, and the water pump.

Furthermore, an inner wall of the U-shaped plate is equipped with two chutes symmetrically, inner walls of the chute are slidingly connected with a slider, and one side of the slider away from the chute is installed on an outer wall of the moving base, by sliding the slider in the chute, it can not only assist the moving base for movements, but also stabilize the position of the moving base.

By adopting the above technical solution, the embodiment of the invention has the following advantages:
1. The invention first transmits the operation paths of adjusting the slide plate at different angles to the controller, and the personnel operates the control panel to control the support jack, the motor, and the electromagnet to start and stop through the controller, the output shaft of the motor drives the stainless steel threaded rod to rotate, the controller first energizes one electromagnet and disconnects the other three electromagnets, which can only make the stainless steel threaded rod rotate in a fixed position inside the inner threaded pipe, and the three inner threaded pipes follow the rotation direction of the stainless steel threaded rod, thus, the position of the support jack can be moved separately. At this time, through the use of the motor and the support jack, it is easy to control the angle of multiple slide plates, each slide plate can change its angle, which is convenient to simulate the landslide movement process in different environments.
2. The invention can realize the control of rainfall area and rainfall intensity through the setting of the water pressure adjustment knob and nozzle switches and has stronger practicability.

The above overview is only for the instructions and the invention is not intended to be limited in any way. In addition to the schematic aspects, embodiments, and characteristics described above, the further aspects, embodiments, and characteristics of the invention will be easy to understand by referring to the attached figures and the following detailed description.

BRIEF DESCRIPTION OF THE DRAWINGS

In order to more clearly explain the implementation of this application or the technical solution in the existing technology, the following will briefly introduce the figures that need to be used in the technical description of the embodiments. Obviously, the drawings in the following description are only some of the embodiments of this application. For ordinary technicians in this field, other drawings can be obtained according to these drawings without paying creative labor.

Marks in the attached figures: 1, support adjustment component; 101, U-shaped plate; 102, support jack; 103, controller; 104, motor; 2, cover plate; 3, nozzle switch; 4. spraying nozzle; 5, stacking plate; 6, high-speed camera; 7, side plate; 8, slide plate; 9, upper roof; 10, outlet pipe; 11, buffer plate; 12, support plate; 13, loose leaves; 14, material cart; 15, slide rail; 16, air storage tank; 17, barometer; 18, air compressor; 19, high-speed cylinder; 20, piston; 21, vent pipe; 22, upper hinge; 23, lower hinge; 24, shaft; 25, water storage tank; 26, water pump; 27, pumping pipe; 28, water pressure meter; 29, water pressure adjustment knob; 30, control panel; 31, moving base; 32, stainless steel threaded rod; 33, installation plate; 34, through hole; 35, electromagnet; 36, chute; 37, slider; 38, inner threaded pipe.

DETAILED DESCRIPTION OF THE EMBODIMENTS

Only some embodiments are briefly described in the following. As technicians in this field can recognize, the described embodiments can be modified in various ways without departing from the spirit or scope of the invention. Therefore, the figures and descriptions are considered to be essentially illustrative rather than restrictive.

The following is a detailed description of the embodiments of the invention in combination with the attached figures.

Figure 1:
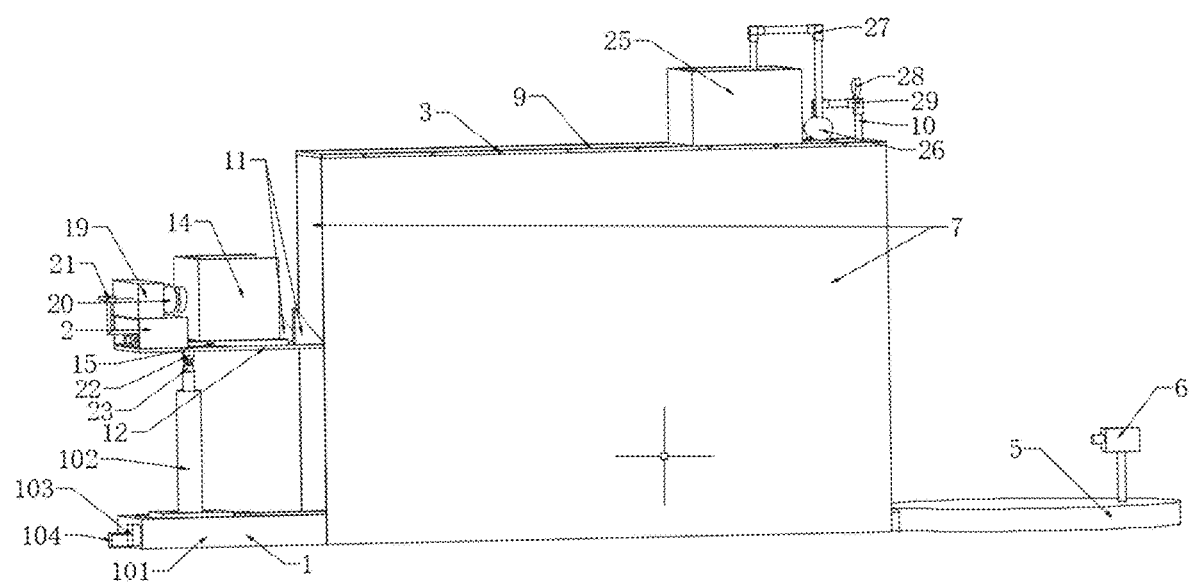
FIG. 1 is a structure diagram of the invention.
Figure 2:
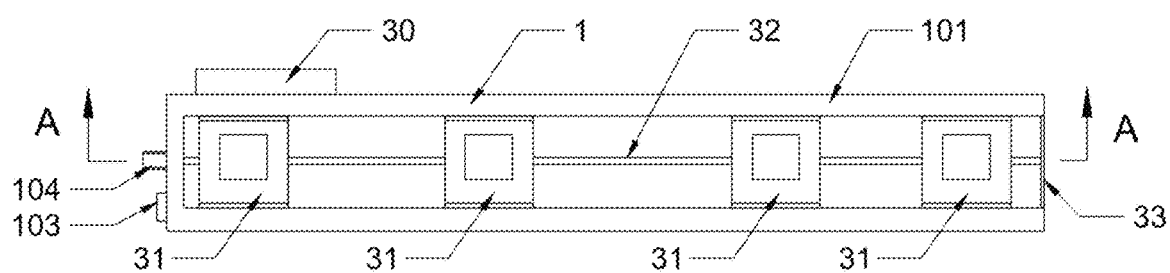
FIG. 2 is a structure diagram of the support adjustment component of the invention.
Figure 3:
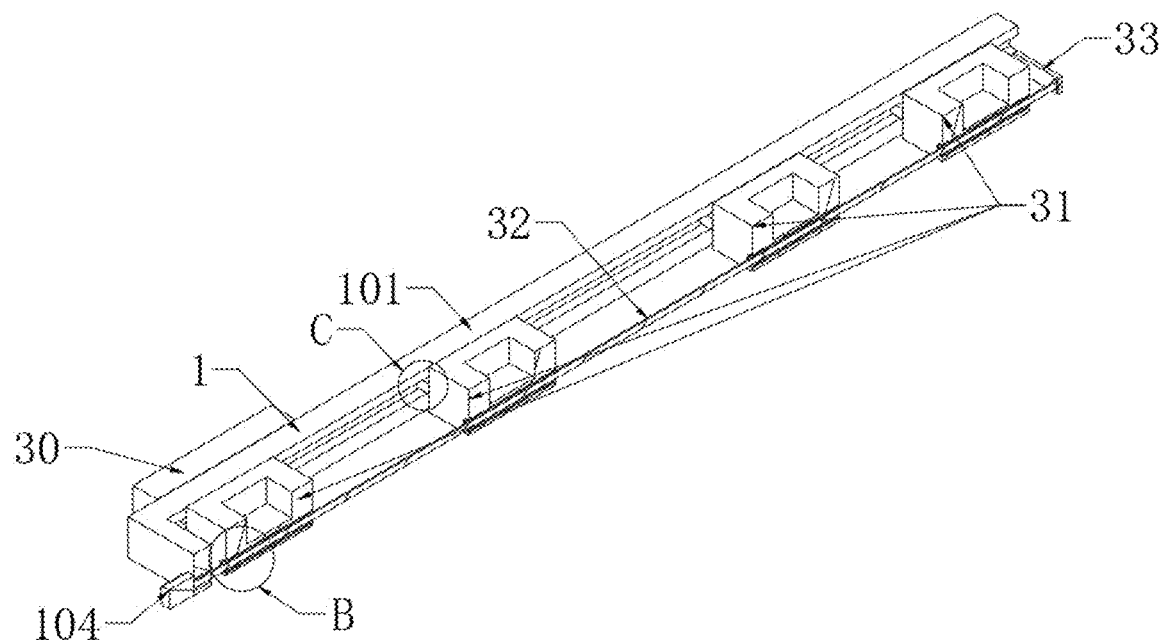
FIG. 3 is an A-A sectional stereo structure diagram of FIG. 2 of the invention.
Figure 4:
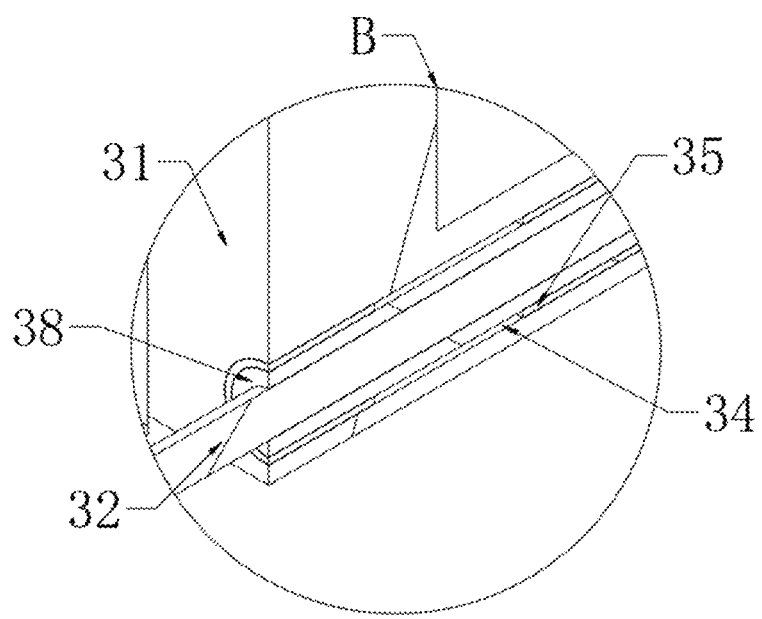
FIG. 4 is an enlarged structure diagram of Zone B in FIG. 3 of the invention.
Figure 5:
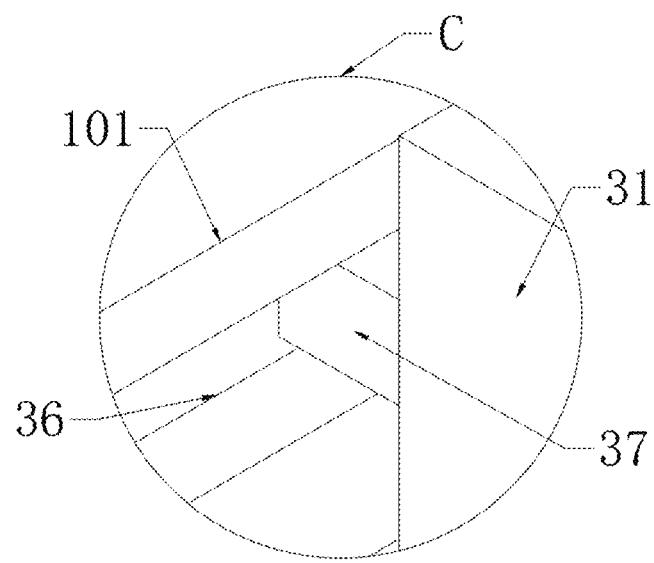
FIG. 5 is an enlarged structure diagram of Zone C in FIG. 3 of the invention.
Figure 6:
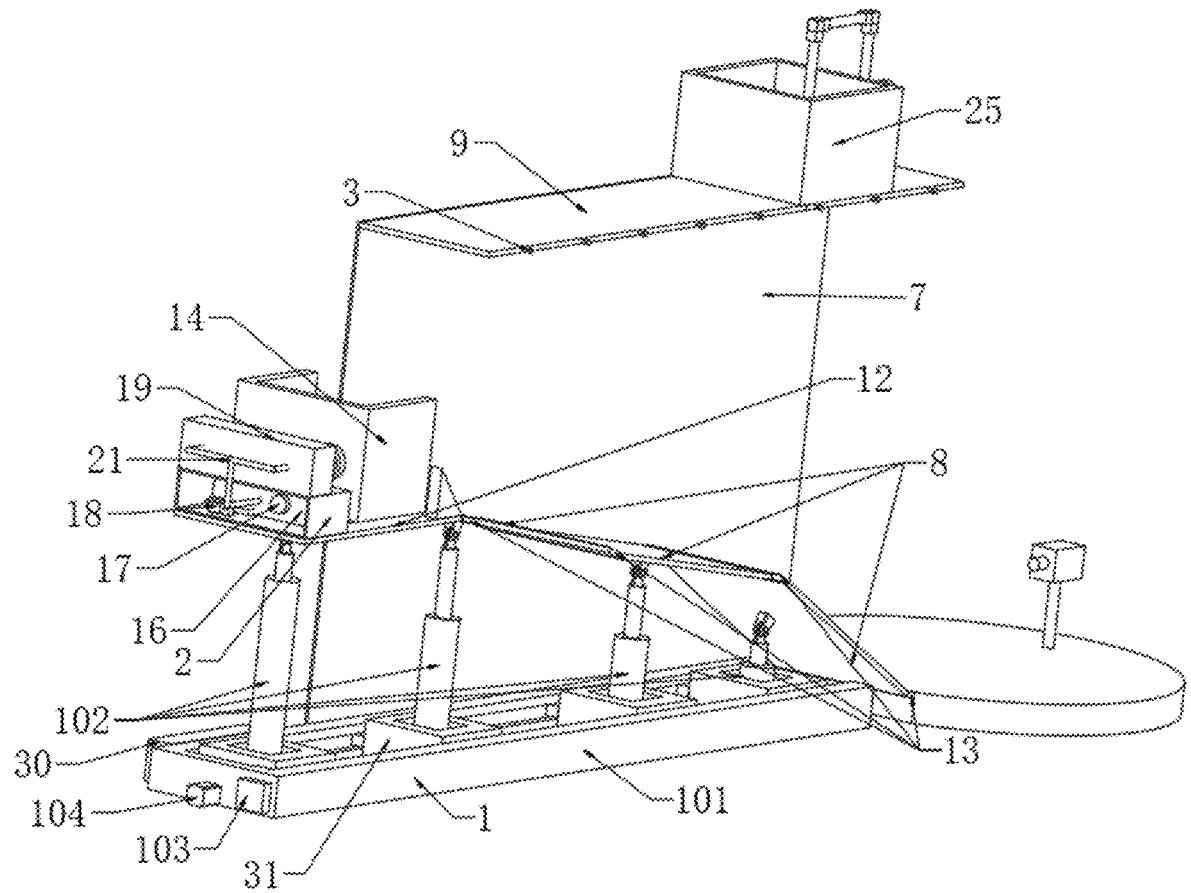
FIG. 6 is an internal structure diagram of the invention.
Figure 7:
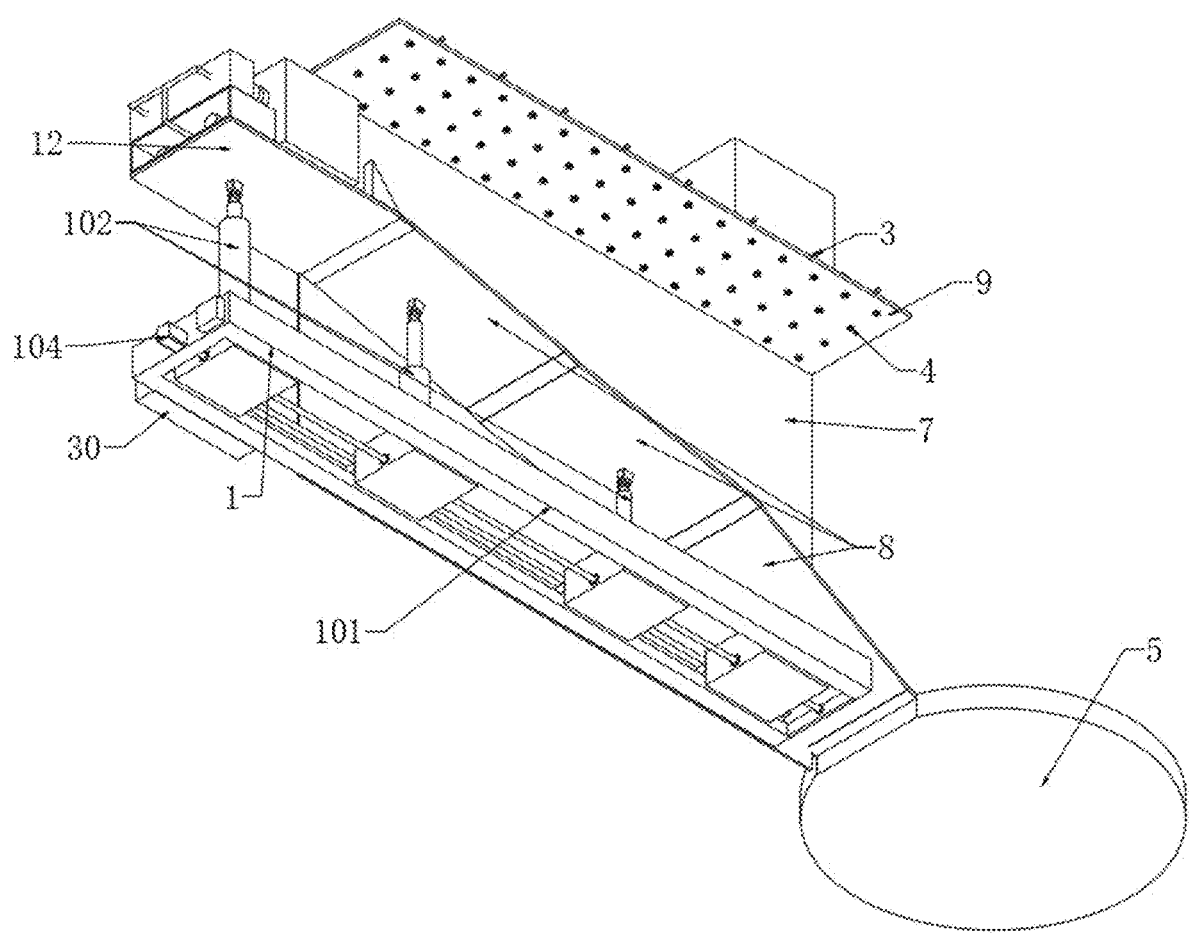
FIG. 7 is an internal bottom view structure diagram of the invention.
Figure 8:
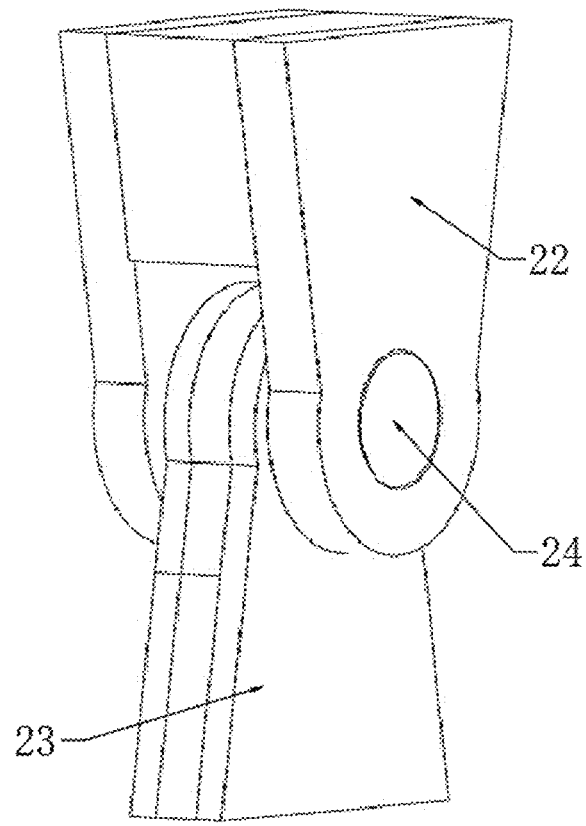
FIG. 8 is a structure diagram of the upper hinge and the lower hinge connection of the invention.
Figure 9:
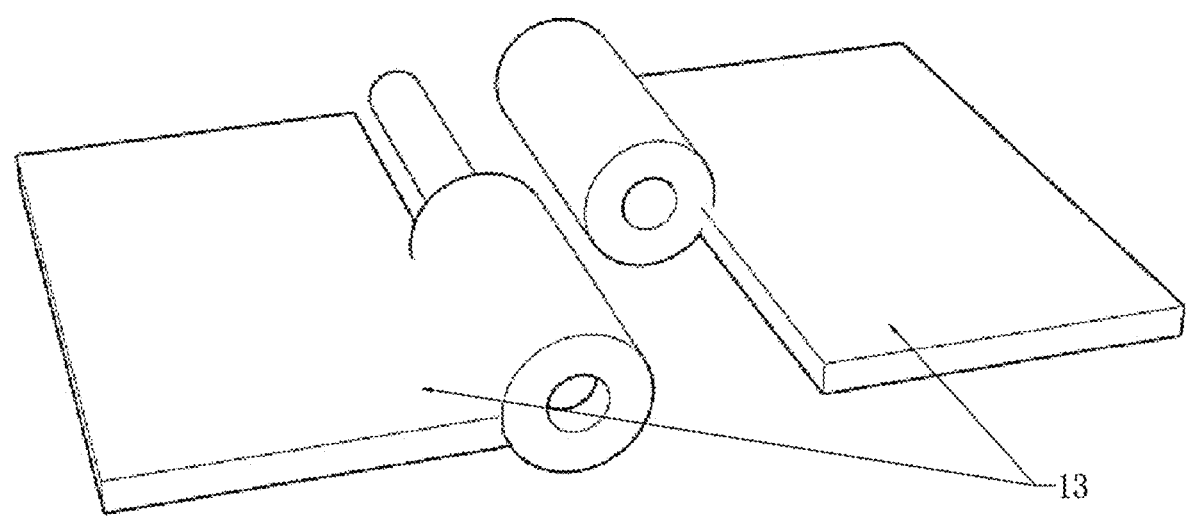
FIG. 9 is a structure diagram of the loose leaves splitting of the invention.
Figure 10:
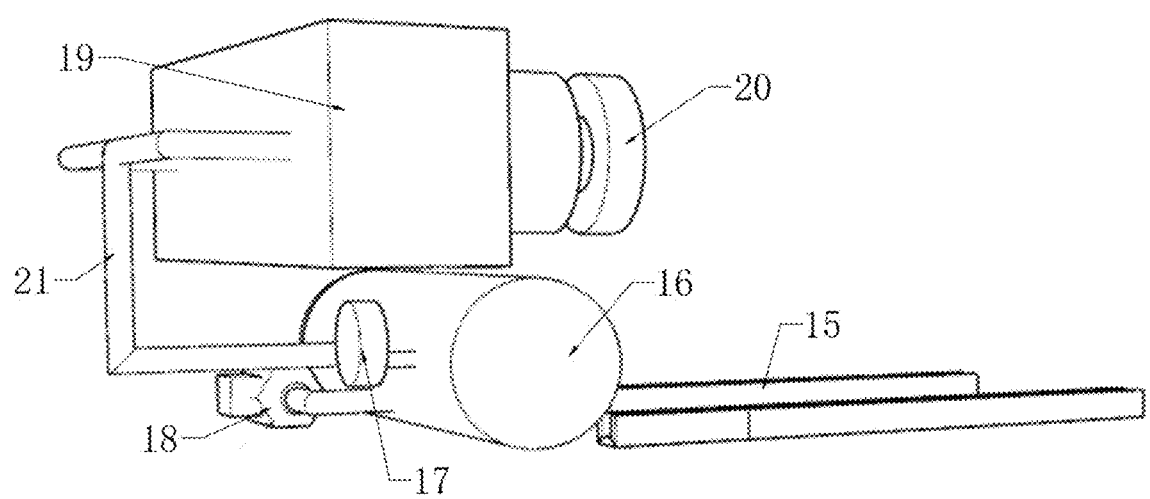
FIG. 10 is a structure diagram of the air storage tank and the high-speed cylinder installation of the invention.
Figure 11:
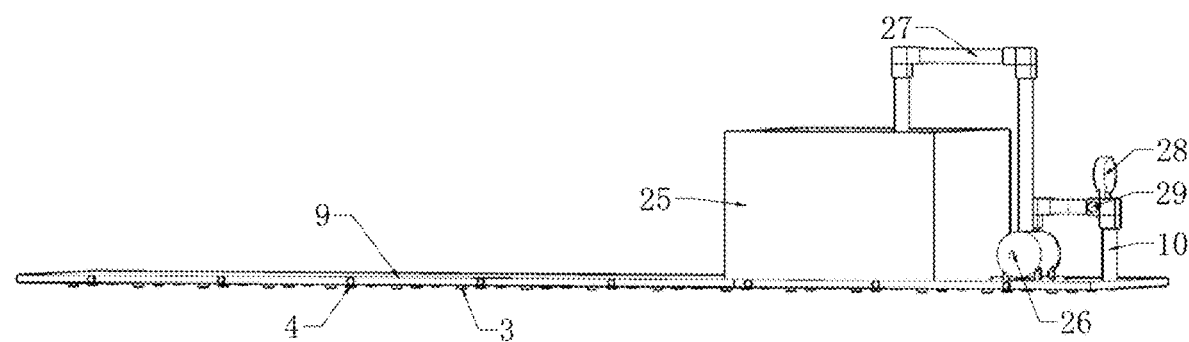
FIG. 11 is a structure diagram of the pump and water storage tank installation of the invention.

As shown in FIG. 1-FIG. 11, the embodiment of the invention provides a high-speed remote landslide simulation test device with a variable angle, comprising a support adjustment component 1, slide plates 8, and loose leaves 13, the support adjustment component 1 includes a U-shaped plate 101, support jacks 102, a controller 103 and a motor 104;

four support jacks 102, three slide plates 8 and four loose leaves 13 are provided, four piston rods of the four support jacks 102 are respectively installed with four lower hinges 23, the inner wall of the lower hinge 23 is installed with the shaft 24, the outer wall of the shaft 24 is installed with the upper hinge 22, the upper surface of the upper hinge 22 is installed with the support plate 12, upper surfaces of the three upper hinges 22 are installed on the lower surfaces of the three slide plates 8 respectively, the adjacent sides of the three slide plates 8 are installed on the outer walls of loose leaves 13, repulsive sides of the two slide plates 8 are installed on the side of the other two loose leaves 13 respectively, another side of one loose leaf 13 is installed on one side of the support plate 12, another side of the another loose leaf 13 is installed with the stacking plate 5, bases of the support jacks 102 are installed with moving bases 31 respectively, one side of the moving base 31 is provided with the through hole 34, the inner wall of the through hole 34 is rotary connected to the inner threaded pipe 38 through a bearing, the inner wall of the through hole 34 is installed with the electromagnet 35, the inner wall of the inner threaded pipe 38 is connected to the stainless steel threaded rod 32, one side of the U-shaped plate 101 is installed with the motor 104, the output shaft of the motor 104 runs through the side of the U-shaped plate 101 and is installed at one end of the stainless steel threaded rod 32, the inner wall of the U-shaped plate 101 is installed with the installation plate 33, the other end of the stainless steel threaded rod 32 is rotary connected to one side of the installation plate 33 through a bearing, one side of the U-shaped plate 101 is installed with the controller 103.

In an embodiment, the outer walls of the three slide plates 8 are symmetrically installed with two side plates 7, the upper surfaces of the two side plates 7 are installed with the upper roof 9, the upper surface of the upper roof 9 is installed with the water storage tank 25 and the water pump 26 respectively, the inlet of the water pump 26 is installed with the pumping pipe 27, one end of the pumping pipe 27 runs through the upper surface of the water storage tank 25, the outlet of the water pump 26 is installed with the outlet pipe 10, one end of the outlet pipe 10 runs through the built-in water pipe network of the upper roof 9, the built-in water pipe network of the upper roof 9 is evenly installed with spraying nozzles 4, and the built-in water pipe network of the upper roof 9 is evenly installed with nozzle switches 3, the outer wall of the outlet pipe 10 is equipped with the water pressure meter 28 and the water pressure adjustment knob 29 respectively, and the spraying nozzles 4 are controlled by adjusting the nozzle switches 3 to spray water to the spraying area on the slide plate 8, and then the pump 26 is opened, and then the water pressure adjustment knob 29 is adjusted to make the pressure value on the water pressure meter 28 reach the set pressure, the water enters the outlet pipe network of the upper roof 9 through the pumping pipe 27 and the outlet pipe 10 from the water storage tank 25, and the rainfall is carried out by the spraying nozzles 4.

In an embodiment, the upper surface of the support plate 12 is installed with the air storage tank 16, the outer wall of the air storage tank 16 is penetrated with the vent pipe 21, one end of the vent pipe 2 is penetrated with the high-speed cylinder 19, one side of the high-speed cylinder 19 is provided with the piston 20, the upper surface of the support plate 12 is installed with the cover plate 2, the upper surface of the cover plate 2 is installed on the lower surface of the high-speed cylinder 19, and the position of the high-speed cylinder 19 is fixed by the setting of the cover plate 2.

In an embodiment, the upper surface of the support plate 12 is symmetrically installed with two slide rails 15, and the inner walls of the two slide rails 15 slides are slidingly connected to the material cart 14, it is convenient for the material cart 14 to move through the setting of the slide rail 15.

In an embodiment, the upper surface of the support plate 12 is symmetrically installed with two buffer plates 11, the material cart 14 is blocked by the buffer plates 11 and stops moving through the setting of the buffer plates 11, and the landslide material in the material cart 14 continues to move forward into the slide plate 8 due to inertia.

In one embodiment, the high-speed camera 6 is installed above the stacking plate 5, the high-speed camera 6 will record the whole process of the landslide through the setting of the high-speed camera 6.

In an embodiment, the outer wall of the air storage tank 16 is equipped with the barometer 17 and the air compressor 18 respectively, the air is inflated into the air storage tank 16 by starting the air compressor 18, when the barometer 17 on the air storage tank 16 shows a set pressure, turn on the regulating switch on the air compressor 18.

In an embodiment, the rear surface of the U-shaped plate 101 is equipped with a control panel 30, through the setting of the control panel 30, it is convenient for personnel to control the controller 103, start and stop the motor 104, the high-speed camera 6, the air compressor 18, the high-speed cylinder 19 and the water pump 26, connect the control panel 30 is electrically connected with the commercial power.

In an embodiment, the inner wall of the U-shaped plate 101 is equipped with two chutes 36 symmetrically, the inner walls of the chutes 26 are slidingly connected with the slider 37, and one side of the slider 37 away from the chute 36 is installed on an outer wall of the moving base, by sliding the slider 37 in the chute 36, it can not only assist the moving base 31 for movements, but also stabilize the position of the moving base 31.

In an embodiment, the material cart 14 has an opening on its side.

In an embodiment, the specifications of the four support jacks 102 are different.

In an embodiment, the side plates 7 are acrylic plates, and the upper roof 9 is an acrylic plate.

In an embodiment, every two rows of spray nozzles 4 are controlled by a nozzle switch 3.

In an embodiment, the material of stainless steel threaded rod 32 is 304 stainless steel.

When the invention is working: the personnel first transmits the operation path of adjusting the slide plate 8 at different angles to the controller 103, and the personnel operates the control panel 30 to control the support jack 102, the motor 104, and the electromagnet 35 to start and stop through the controller 103, when it is necessary to move the position of the moving base 31, start the motor 104, the output shaft of the motor 104 drives the stainless steel threaded rod 32 to rotate, the controller 103 first energizes one electromagnet 35 and disconnects the other three electromagnets 35, which can only make the stainless steel threaded rod 32 rotate in a fixed position inside the inner threaded pipe 38, and the three inner threaded pipes 38 follow the rotation direction of the stainless steel threaded rod 32, thus, the position of the support jack 102 can be moved separately. At this time, through the use of the motor 104 and the support jack 102, the angle and height of the slide plates 8 and the support plate 12 are adjusted respectively, after the shape setting of the slide plate 8 is completed, the nozzle switches 3 are adjusted to control the spray nozzles 4 to spray water to set the spray area on the slide plate 8, and then the pump 26 is started, and then the water pressure adjustment knob 29 is adjusted to make the pressure value on the water pressure meter 28 reach the set pressure, the water enters the outlet pipe network of the upper roof 9 through the pumping pipe 27 and the outlet pipe 10 from the water storage tank 25, and the rainfall is carried out by the spray nozzles 4, after the setting is completed, the filling material is filled into the material cart 14, and the air is inflated into the air storage tank 16 by starting the air compressor 18, when the barometer 17 on the air storage tank 16 is shown as the set pressure, the adjustment switch on the air compressor 18 is turned on, so that the high-speed cylinder 19 drives the piston 20 to move forward under the action of air pressure, and the piston 20 drives the material cart 14 to move forward along the slide rail 15, when the material cart 14 reaches the buffer plate 11, the material cart 14 is blocked by the buffer plate 11 and stopped, the landslide material in the material cart 14 continues to enter the slide plate 8 due to inertia, in the process of landslide simulation, the high-speed camera 6 will record the whole process of landslide. Finally, the landslide material accumulates on the stacking plate 5, and the landslide simulation is completed.

The above-mentioned description is only the specific embodiment of the invention, which does contribute to any limitation to the protection scope of the invention. Any technical personnel familiar with the technical field of the invention can easily think of its various changes or replacements within the technical scope revealed by the invention, which should be covered within the protection scope of the invention. Therefore, the scope of protection of the invention shall be subject to the scope of protection of the claims.

What is claimed is:

1. A high-speed remote landslide simulation test device with a variable angle, comprising a support adjustment component, three slide plates, and four loose leaves, wherein the support adjustment component includes a U-shaped plate, four support jacks, a controller, and a motor;

four piston rods of the four support jacks are respectively installed with four lower hinges, inner walls of the four lower hinges are installed with four shafts, respectively, outer walls of the four shafts are installed with four upper hinges, respectively, including a first upper hinge, a second upper hinge, a third upper hinge and a fourth upper hinge, an upper surface of a first upper hinge is installed with a support plate, upper surfaces of the second upper hinge, the third upper hinge and the fourth upper hinge are installed on lower surfaces of the three slide plates, respectively;

three slide plates include a first slide plate, a second slide plate, and a third slide plate, adjacent sides of the first slide plate and the second slide plate are installed on an outer wall of a second loose leaf, adjacent sides of the second slide plate and the third slide plate are installed on an outer wall of a third loose leaf, repulsive sides of the first slide plate and the third slide plate are installed on first sides of a first loose leaf and a fourth loose leaf, respectively, a second side of the first loose leaf is installed on one side of the support plate, a second side of the fourth loose leaf is installed with a stacking plate;

bases of the four support jacks are installed with four moving bases, respectively, one side of each of the four moving bases is provided with a through hole, an inner wall of the through hole is rotatably connected to an inner threaded pipe through a first bearing, the inner wall of the through hole is installed with an electromagnet, an inner wall of the inner threaded pipe is connected to a stainless steel threaded rod, one side of the U-shaped plate is installed with a motor, an output shaft of the motor runs through the side of the U-shaped plate and is installed at a first end of the stainless steel threaded rod, an inner wall of the U-shaped plate is installed with an installation plate, a second end of the stainless steel threaded rod is rotatably connected to one side of the installation plate through a second bearing, one side of the U-shaped plate is installed with the controller.

2. The high-speed remote landslide simulation test device according to claim 1, wherein outer walls of the three slide plates are symmetrically installed with two side plates, upper surfaces of the two side plates are installed with an upper roof, an upper surface of the upper roof is installed with a water storage tank and a water pump, an inlet of the water pump is installed with a pumping pipe, one end of the pumping pipe runs through an upper surface of the water storage tank, an outlet of the water pump is installed with an outlet pipe, one end of the outlet pipe runs through a built-in water pipe network of the upper roof, the built-in water pipe network of the upper roof is evenly installed with spraying nozzles, and the built-in water pipe network of the upper roof is evenly installed with nozzle switches, an outer wall of the outlet pipe is equipped with a water pressure meter and a water pressure adjustment knob, and the spraying nozzles are controlled by adjusting the nozzle switches to spray water to a spraying area on the three slide plates.

3. The high-speed remote landslide simulation test device according to claim 1, wherein an upper surface of the support plate is installed with an air storage tank, an outer wall of the air storage tank is penetrated with a vent pipe, one end of the vent pipe is penetrated with a high-speed cylinder, one side of the high-speed cylinder is provided with a piston, the upper surface of the support plate is installed with a cover plate, an upper surface of the cover plate is installed on a lower surface of the high-speed cylinder, and a position of the high-speed cylinder is fixed by setting the cover plate.

4. The high-speed remote landslide simulation test device according to claim 1, wherein an upper surface of the support plate is symmetrically installed with two slide rails and inner walls of the two slide rails slides are slidingly connected to a material cart, and the material cart is configured to move through the two slide rails.

5. The high-speed remote landslide simulation test device according to claim 1, wherein an upper surface of the support plate is symmetrically installed with two buffer plates, a material cart is blocked by the two buffer plates and stops moving through setting the two buffer plates, and a landslide material in the material cart continues to move forward into the three slide plates due to inertia.

6. The high-speed remote landslide simulation test device according to claim 1, wherein a high-speed camera is installed above the stacking plate, the high-speed camera is configured to record a whole process of a landslide.

7. The high-speed remote landslide simulation test device according to claim 3, wherein the outer wall of the air storage tank is equipped with a barometer and an air compressor, air is inflated into the air storage tank by starting the air compressor, when the barometer on the air storage tank shows a set pressure, a regulating switch on the air compressor is turned on.

8. The high-speed remote landslide simulation test device according to claim 1, wherein a rear surface of the U-shaped plate is equipped with a control panel, the control panel is configured for personnel to control the controller, start and stop the motor, a high-speed camera, an air compressor, a high-speed cylinder, and a water pump.

9. The high-speed remote landslide simulation test device according to claim 1, wherein an inner wall of the U-shaped plate is equipped with two chutes symmetrically, inner walls of the two chutes are slidingly connected with sliders, and one side of each of the sliders away from the two chutes is installed on an outer wall of each of the four moving bases, the sliders sliding in the chute are configured to assist the four moving bases for movements, and stabilize a position of the four moving bases.

* * * * *